US010576226B2

(12) United States Patent
Kwok et al.

(10) Patent No.: US 10,576,226 B2
(45) Date of Patent: Mar. 3, 2020

(54) AIR DELIVERY SYSTEM

(71) Applicant: ResMed Pty Ltd, Bella Vista, New South Wales (AU)

(72) Inventors: Philip Rodney Kwok, Sydney (AU); Muditha Pradeep Dantanarayana, Sydney (AU); Mark Bertinetti, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 847 days.

(21) Appl. No.: 15/179,381

(22) Filed: Jun. 10, 2016

(65) Prior Publication Data

US 2016/0279360 A1  Sep. 29, 2016

Related U.S. Application Data

(60) Continuation of application No. 13/067,081, filed on May 6, 2011, now abandoned, which is a division of (Continued)

(51) Int. Cl.
*A61M 16/00* (2006.01)

(52) U.S. Cl.
CPC . *A61M 16/0057* (2013.01); *A61M 2205/3334* (2013.01); *A61M 2205/35* (2013.01); *A61M 2205/505* (2013.01)

(58) Field of Classification Search
CPC .. A61M 16/0057; A61M 11/00; A61M 15/00; A61M 2205/17; A61M 2205/3334;
(Continued)

(56) References Cited

U.S. PATENT DOCUMENTS 4,323,064 A   4/1982  Hoenig
4,340,044 A   7/1982  Levy
(Continued)

FOREIGN PATENT DOCUMENTS

CN   1440302    9/2003
WO   01/32069   5/2001
(Continued)

OTHER PUBLICATIONS

Decision on Reexamination dated Mar. 18, 2015 in Chinese Application No. 200710087962.5, with English translation (22 pages).
(Continued)

*Primary Examiner* — Steven O Douglas
(74) *Attorney, Agent, or Firm* — Nixon & Vanderhye, P.C.

(57) ABSTRACT

An air delivery system includes a controllable flow generator, a primary controller, and an auxiliary controller. The flow generator is operable to generate a supply of pressurized breathable gas to be provided to a patient for treatment. The primary controller is associated with at least one primary control feature to select at least a first aspect of operation of the flow generator. The auxiliary controller is associated with at least one auxiliary control feature to select at least a second aspect of operation of the flow generator. The second aspect selected by the auxiliary controller is different than the first aspect selected by the primary controller. The primary and auxiliary controllers may be interchangeably usable to control operation of the flow generator.

16 Claims, 5 Drawing Sheets

Related U.S. Application Data application No. 11/494,522, filed on Jul. 28, 2006, now Pat. No. 7,958,892.

(60) Provisional application No. 60/703,457, filed on Jul. 29, 2005.

(58) Field of Classification Search
CPC ........ A61M 2205/35; A61M 2205/505; A61M 2230/201
See application file for complete search history.

(56) References Cited

U.S. PATENT DOCUMENTS

| | | |
|---|---|---|
| 4,944,310 A | 7/1990 | Sullivan et al. |
| 5,192,042 A | 3/1993 | Wotring et al. |
| 5,199,424 A | 4/1993 | Sullivan et al. |
| 5,241,592 A | 8/1993 | Carlson et al. |
| 5,503,146 A | 4/1996 | Froehlich |
| 5,522,382 A | 6/1996 | Sullivan et al. |
| 5,535,738 A | 7/1996 | Estes et al. |
| 5,551,419 A | 9/1996 | Froehlich |
| 5,560,353 A | 10/1996 | Willemot et al. |
| 5,598,838 A | 2/1997 | Servidio et al. |
| 5,615,109 A | 3/1997 | Eder |
| 5,692,497 A | 12/1997 | Schnitzer et al. |
| 5,704,345 A | 1/1998 | Berthon-Jones |
| 5,794,625 A | 8/1998 | McCarley et al. |
| 5,823,651 A | 10/1998 | Helot et al. |
| 5,881,723 A | 3/1999 | Wallace et al. |
| 6,000,608 A | 12/1999 | Dorf |
| 6,029,665 A | 2/2000 | Berthon-Jones |
| 6,105,575 A | 8/2000 | Estes et al. |
| 6,138,675 A | 10/2000 | Berthon-Jones |
| 6,158,433 A | 12/2000 | Ong |
| 6,349,724 B1 | 2/2002 | Burton et al. |
| 6,363,933 B1 | 4/2002 | Berthon-Jones |
| 6,543,449 B1 | 4/2003 | Woodring et al. |
| 6,609,517 B1 | 8/2003 | Estes et al. |
| 6,705,315 B2 | 3/2004 | Sullivan et al. |
| 6,886,948 B2 | 5/2005 | Nakano |
| 6,983,126 B1 | 1/2006 | Saalman |
| 7,128,069 B2 | 10/2006 | Farrugia et al. |
| 7,188,621 B2 | 3/2007 | Devries et al. |
| 7,191,780 B2 | 3/2007 | Faram |
| 7,225,809 B1 | 6/2007 | Bowen |
| 7,469,698 B1 | 12/2008 | Childers et al. |
| 7,588,031 B2 | 9/2009 | Truschel et al. |
| 7,779,834 B2 | 8/2010 | Calluaud et al. |
| 7,942,823 B2 | 5/2011 | Wright et al. |
| 7,958,892 B2 | 6/2011 | Kwok et al. |
| 8,172,766 B1 | 5/2012 | Kayyali et al. |
| 8,499,761 B2 | 8/2013 | Jorczak et al. |
| 8,640,697 B2 | 2/2014 | Reed |
| 9,566,403 B2 | 2/2017 | Reed |
| 2003/0066529 A1 | 4/2003 | Truschel et al. |
| 2003/0213489 A1 | 11/2003 | Mechlenburg et al. |
| 2004/0054587 A1 | 3/2004 | Dev et al. |
| 2004/0074496 A1 | 4/2004 | Hayashi et al. |
| 2005/0061318 A1 | 3/2005 | Faram |
| 2005/0178384 A1 | 8/2005 | Martin et al. |
| 2005/0211761 A1 | 9/2005 | Antilla et al. |
| 2006/0084877 A1 | 4/2006 | Ujhazy et al. |
| 2006/0112959 A1 | 6/2006 | Mechlenburg et al. |
| 2006/0124128 A1 | 6/2006 | Deane et al. |
| 2006/0130836 A1 | 6/2006 | Wixey |
| 2006/0237014 A1 | 10/2006 | Makinson |
| 2007/0023045 A1 | 2/2007 | Kwok et al. |
| 2007/0193583 A1 | 8/2007 | Reed |
| 2007/0287895 A1 | 12/2007 | Brown |
| 2010/0114218 A1 | 5/2010 | Heath |
| 2010/0147301 A1 | 6/2010 | Kwok et al. |
| 2010/0236552 A1 | 9/2010 | Kwok et al. |
| 2011/0192400 A9 | 8/2011 | Burton et al. |
| 2011/0240024 A1 | 10/2011 | Kwok et al. |
| 2014/0116438 A1 | 5/2014 | Reed |

FOREIGN PATENT DOCUMENTS

| | | |
|---|---|---|
| WO | 2002/002169 | 1/2002 |
| WO | 2002/018002 | 3/2002 |
| WO | 2003/024335 | 3/2003 |
| WO | 2004/067070 | 8/2004 |
| WO | 2004/112680 | 12/2004 |
| WO | 2005/002655 A1 | 1/2005 |
| WO | 2005/028009 | 3/2005 |
| WO | 2005/063323 | 7/2005 |
| WO | 2005/065757 | 7/2005 |
| WO | 2005/077447 | 8/2005 |
| WO | 2005/099798 | 10/2005 |

OTHER PUBLICATIONS

Notification of Reexamination dated Dec. 26, 2014 in Chinese Application No. 200710087962.5, with English Translation (18 pages).
Notification of the First Office Action dated Jan. 7, 2015 in Chinese Application No. 201310228831.X, with English Translation (14 pages).
Notification of the Second Office Action dated Sep. 16, 2015 in Chinese Application No. 201310228831.X, with English Translation (9 pages).
Notification of the Third Office Action dated Apr. 1, 2016 issued in Chinese Application No. 201310228831.X with English translation (21 pages).
Office Action for U.S. Appl. No. 13/067,081, dated Aug. 11, 2014 (7 pages).
Office Action for U.S. Appl. No. 13/067,081, dated Jan. 5, 2015 (6 pages).
Office Action for U.S. Appl. No. 13/067,081, dated Feb. 4, 2015 (7 pages).
Office Action for U.S. Appl. No. 13/067,081, dated Jun. 23, 2015 (8 pages).
Office Action for U.S. Appl. No. 13/067,081, dated Oct. 2, 2015 (7 pages).
Office Action for U.S. Appl. No. 13/067,081, dated Mar. 10, 2016 (8 pages).
Office Action for U.S. Appl. No. 14/148,055, dated Feb. 29, 2016 (18 pages).
Office Action dated Aug. 30, 2011 in Chinese Application No. 200710087962.5 (with translation).
Office Action dated Mar. 31, 2012 in Chinese Application No. 200710087962.5 (with translation).
Office Action dated May 5, 2011 in Chinese Application No. 200710087962.5 (with translation).
Office Action dated Oct. 12, 2010 in Chinese Application No. 200710087962.5 (with translation).
U.S. Appl. No. 60/505,718, filed Sep. 25, 2003.
U.S. Appl. No. 60/624,951, filed Nov. 2004.
U.S. Appl. No. 60/625,878, filed Nov. 2004.
U.S. Appl. No. 60/656,880, filed Mar. 1, 2005.
U.S. Appl. No. 60/703,457, filed Jul. 29, 2005.
U.S. Appl. No. 60/707,950, filed Aug. 15, 2005.
U.S. Appl. No. 60/774,222, filed Feb. 17, 2006.
Office Action dated Jun. 22, 2016, U.S. Appl. No. 14/148,055, 10 pages.
Office Action dated Jul. 31, 2019, U.S. Appl. No. 15/393,058, 27 pages.
Decision of Rejection dated Sep. 30, 2016, issued in Chinese Application No. 201310228831X and English translation, 16 pages.
Notification of the First Office Action dated Feb. 22, 2017, issued in Chinese Application No. 201510347413.1 and English translation, 20 pages.
Notification of the Second Office Action dated Apr. 2, 2018, issued in Chinese Application No. 201510347413.1 and English translation, 10 pages.
Decision of Rejection dated Nov. 30, 2018, issued in Chinese Application No. 201510347413.1 and English translation, 16 pages.
U.S. Appl. No. 11/707,160, filed Feb. 16, 2007.

AIR DELIVERY SYSTEM

CROSS REFERENCE TO RELATED APPLICATION

The present application is a continuation of U.S. patent application Ser. No. 13/067,081, filed May 6, 2011, now pending, which is a divisional of U.S. patent application Ser. No. 11/494,522, filed on Jul. 28, 2006, now U.S. Pat. No. 7,958,892, which claims priority to U.S. Provisional Application Ser. No. 60/703,457, filed Jul. 29, 2005, each of which is incorporated into the present application by reference in its entirety.

FIELD OF THE INVENTION

The present invention relates to a flow generator used in the treatment, e.g., of Sleep Disordered Breathing (SDB) with CPAP or Non-Invasive Positive Pressure Ventilation (NIPPV).

BACKGROUND OF THE INVENTION

A flow generator typically includes a housing with an integrated control panel for controlling the delivery of pressurized air to be provided to a patient for treatment. Treatment may be provided in various forms, from both simple CPAP systems to more complex non-invasive positive pressure ventilation (NIPPV), such as a Bi-level pressurized gas delivery system. The flow generator may be structured to administer only one form of treatment, or the flow generator may be structured to administer various forms of treatment.

Regardless of the type of flow generator, the control panel of the flow generator allows a clinician and/or patient to adjust the operating parameters or settings of the flow generator for a particular treatment. When the treatment is more complex, the control panel may be relatively advanced with multiple menus and features. If the operating parameters for a treatment are not appropriately selected, e.g., selected by an untrained patient, the treatment may be ineffective and/or harmful to the patient, or the patient simply will not use the apparatus.

Known control panels provide security codes to prevent the patient from inappropriately adjusting certain operating parameters. However, if the patient learns the security codes and/or the security codes are not implemented, the patient can access the same operating parameters as a trained clinician. Therefore, a need has developed in the art to provide improvements to known flow generators to prevent inappropriate selection of operating parameters.

SUMMARY OF THE INVENTION

One aspect of the invention is directed towards an air delivery system including a flow generator with interchangeable controllers to control operation of the flow generator, wherein one of the controllers includes basic features for use by a patient and the other of the controllers includes more advanced features for use by a trained clinician.

Another aspect of the invention relates to an air delivery system including a controllable flow generator, a primary controller, and an auxiliary controller. The flow generator is operable to generate a supply of pressurized breathable gas to be provided to a patient for treatment. The primary controller is associated with at least one primary control feature to select at least a first aspect of operation of the flow generator. The auxiliary controller is associated with at least one auxiliary control feature to select at least a second aspect of operation of the flow generator. The second aspect selected by the auxiliary controller is different than the first aspect selected by the primary controller. The primary and auxiliary controllers may be interchangeably usable to control operation of the flow generator.

Yet another aspect of the invention relates to an air delivery system including a controllable flow generator and a primary controller. The flow generator is operable to generate a supply of pressurized breathable gas to be provided to a patient for treatment. The primary controller is detachably mountable to the flow generator. The controller is associated with at least one primary control feature to select or control at least a first aspect of operation of the flow generator.

Yet another aspect of the invention relates to an air delivery system including a flow generator and a primary controller. The flow generator is structured to generate a supply of pressurized breathable gas. The flow generator is programmed with basic flow generator control features and advanced flow generator control features. The primary controller is only in communication with at least one of the basic control features of the flow generator.

Yet another aspect of the invention relates to an air delivery system including a flow generator and a blood glucose monitor. The flow generator is operable to generate a supply of pressurized breathable gas to be provided to a patient for treatment. The blood glucose monitor is detachably mountable to the flow generator.

Yet another aspect of the invention relates to an air delivery system including a controllable flow generator operable to generate a supply of pressurized breathable gas to be provided to a patient for treatment. The flow generator is operable in a continuous pressure delivery mode and a variable pressure delivery mode. At least one controller is configured to operate the flow generator in one of the continuous pressure delivery mode or the variable pressure delivery mode.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
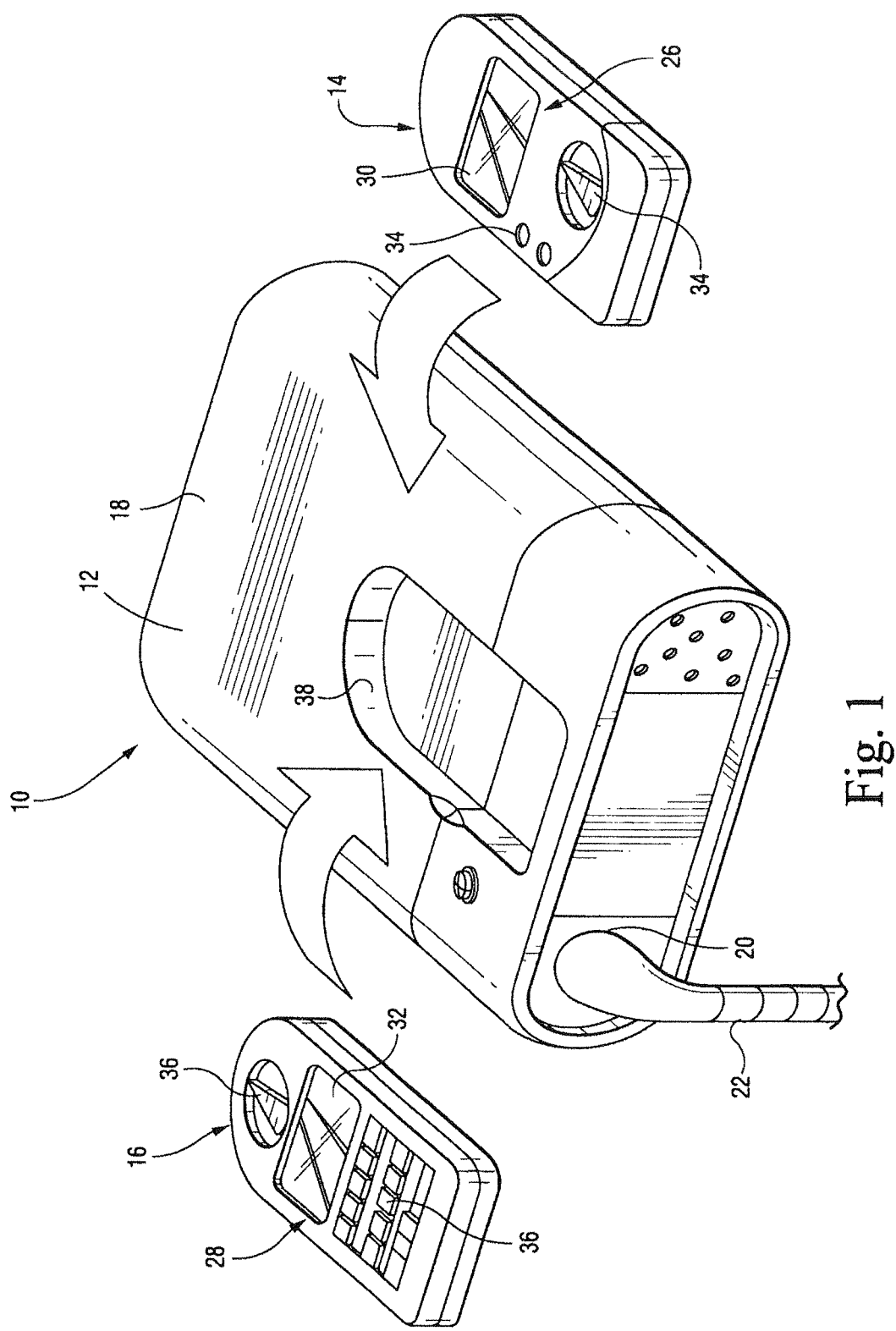
FIG. 1 is a perspective view of an air delivery system constructed according to an embodiment of the present invention, the air delivery system including a flow generator and interchangeable controllers.

FIG. 1 illustrates an air delivery system 10 constructed according to an embodiment of the present invention. The air delivery system 10 includes a controllable flow generator 12 operable to generate a supply of pressurized breathable air to be provided to a patient for treatment, e.g., of Sleep Disordered Breathing (SDB) with CPAP or Non-Invasive Positive Pressure Ventilation (NIPPV).

The air delivery system 10 provides interchangeable controllers 14 and 16 to control operation of the flow generator 12. One controller 14 includes basic features for use by the patient, and the other controller 16 includes more advanced features for use by a trained clinician. This arrangement prevents the patient from selecting inappropriate operating parameters of the flow generator 12, as discussed in greater detail below.

Flow Generator

As shown in FIG. 1, the flow generator 12 includes a housing 18 that supports a blower. As is known in the art, the blower is operable to draw a supply of air into the housing through one or more intake openings and provide a pressurized flow of air at an outlet 20.

Figure 2:
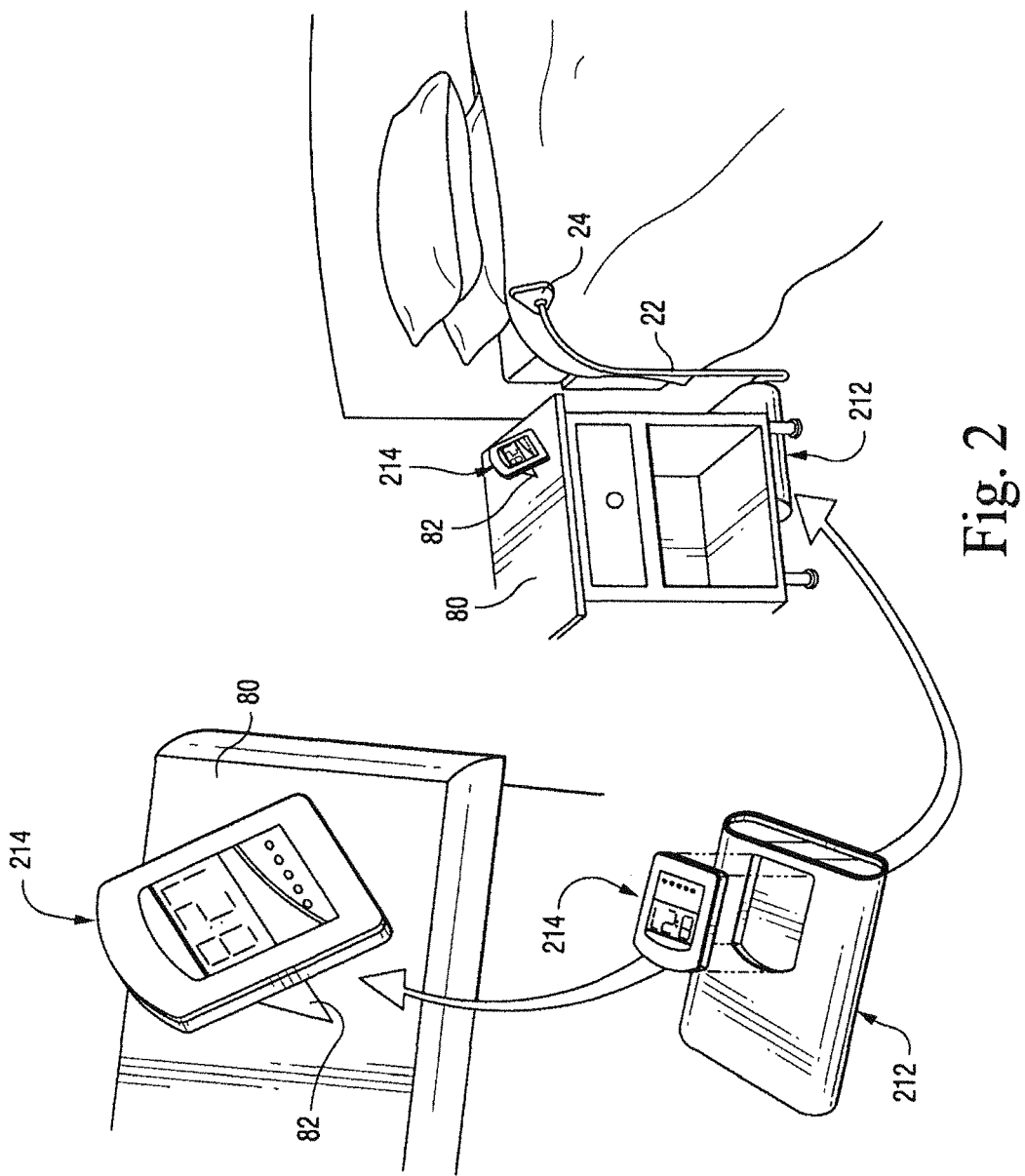
FIG. 2 is a perspective view of an air delivery system constructed according to another embodiment of the present invention.

The supply of pressurized air is delivered to the patient via an air delivery conduit 22 that includes one end coupled to the outlet 20 of the flow generator 12 and an opposite end coupled to a patient interface 24 (e.g., see FIG. 2).

The patient interface 24 comfortably engages the patient's face and provides a seal. The patient interface 24 may have any suitable configuration as is known in the art, e.g., full-face mask, nasal mask, oro-nasal mask, mouth mask, nasal prongs, etc. Also, any suitable headgear arrangement may be utilized to comfortably support the patient interface in a desired position on the patient's face.

Interchangeable Primary and Auxiliary Controllers

As noted above, the flow generator 12 is controllable by interchangeable controllers 14 and 16. Both controllers 14 and 16 are compatible with the flow generator 12 and may be interchangeably useable to control operation of the flow generator 12.

Also, a removable or interchangeable controller allows the controller to be installed into a replacement flow generator without having to reprogram as patient information may be stored in the removable controller.

As shown in FIG. 1, each of the controllers 14 and 16 is in the form of a hand-held device that may be wirelessly communicated with the flow generator 12. A suitable protocol controls whether the controller 14 or controller 16 operates to select operational aspects of the flow generator. For example, a "registration" button may be provided on the flow generator 12 that is configured to learn the operating frequency of a controller, e.g., radio frequency wireless technology.

Each controller 14 and 16 is operable to receive input, e.g., input signals, and to control operation of the flow generator 12 based on input signals. The controllers 14, 16 include a control panel 26, 28 that provides a display screen 30, 32 and one or more control features 34, 36, e.g., rotatable knob and buttons, respectively, that provide input signals. The control features 34, 36 of each controller 14, 16 may be manually selected to adjust operating parameters of the flow generator 12. As illustrated, the housing 18 of the flow generator 12 provides a recess 38, e.g., in the top wall, adapted to removably hold a selected one of the controllers 14, 16.

In the illustrated embodiment, one controller 14 is a primary controller that is operable to receive input signals from primary control features 34 to control operation of the flow generator 12. That is, the primary controller 14 includes relatively basic control features 34 adapted to control relatively basic aspects of the flow generator 12. The primary controller 14 is adapted for use by one who is relatively untrained, e.g., patient, to prevent the control of advanced aspects of the flow generator 12 that could alter the effectiveness of the treatment and/or cause harm to the patient. Also, the problem of patients being able to learn how to enter a program mode is ameliorated over current devices.

The other controller 16 is an auxiliary controller that is operable to receive input signals from auxiliary control features 36 to control operation of the flow generator 12. That is, the auxiliary controller 16 includes relatively advanced control features 36 adapted to control relatively advanced aspects of the flow generator 12. The auxiliary controller 16 may also include basic control features similar to those provided by the primary controller 14. In the illustrated embodiment, the auxiliary controller 16 provides more control features than the primary controller 14. Regardless, the auxiliary controller 16 provides control features that are different than the basic features provided by the primary controller 14, thereby allowing control of aspects not accessible by the primary controller 14. The auxiliary controller 16 is adapted for use by one, e.g., clinician, who is relatively trained in breathing treatment to allow control of advanced aspects of the flow generator 12 in order to tailor and/or adjust treatment provided to the patient. Furthermore, a service technician may have a controller version that allows the service technician to diagnose motor and/or circuit board operations, perform testing, and/or service the flow generator.

Thus, the flow generator 12 provides separate clinical and patient use. In an embodiment, the primary controller 14 is usable by a patient to operate the flow generator 12 in a manner that has been already pre-programmed by a trained clinician. This facilitates operation, and prevents the patient from changing the operating parameters.

The trained clinician pre-programs the flow generator 12 with the auxiliary controller 16. As noted above, the auxiliary controller 16 allows access to advanced features, e.g., via clinical menus, to program the flow generator 12 for a particular treatment. The auxiliary controller 16 may allow access to a memory that stores preferred operating parameters for a variety of treatments. The auxiliary controller 16 can then control the flow generator 12 based on the stored operating parameters in the memory for the selected treatment. Alternatively, the operating parameters for a selected treatment may be entered manually through the auxiliary controller 16. Further, the auxiliary controller 16 may allow access to a log of the patient's use for tracking purposes. This separate clinical/patient arrangement of the system allows the clinician to monitor operation and adjust operating parameters of the flow generator 12 without patient interference.

In an embodiment, the relatively basic controller 14 may be configured to control start, stop, and delay timer operations. When the flow generator 12 is registered with the relatively advanced controller 16, the relatively basic controller 14 still functions but the relatively advanced controller 16 can override the relatively basic controller 14. The relatively advanced controller 16 may also have patient setup and diagnostic functions such as adjusting pressure, checking patient compliance, and/or usage data. The relatively advanced controller 16 may be deregistered from the flow generator 12 once the flow generator 12 has been operated with the relatively basic controller 14 for more than one sleep session.

It is noted that a flow generator 12 may be controllable by a single controller or multiple controllers, with each of controllers having control features suitable for a particular treatment. For example, one controller may be usable to operate the flow generator as a simple CPAP device, one controller may be usable to operate the flow generator as a more advanced VPAP device, etc. Thus, the flow generator may be upgraded by communicating a new controller with the flow generator 12.

"Plug and Play" Arrangement

The air delivery system may provide a "plug and play" arrangement wherein the patient can simply communicate a controller with the flow generator 12 to automatically configure the flow generator 12 for a particular treatment. For example, the system may include controller to operate the flow generator as a CPAP device, and a controller to operate the flow generator as a VPAP device. Each controller would have a unique identifying feature so that the flow generator 12 can recognize which controller is communicated to the flow generator 12. Moreover, the controller can optimize operation of the flow generator 12 for the specified treatment.

Controller with Clock/Alarm

As noted above, the controller 14, 16 for the flow generator 12 may be wirelessly communicated with the flow generator 12. This arrangement allows the patient and/or clinician to easily adjust operating parameters of the flow generator 12 without being adjacent to the flow generator 12. Moreover, this arrangement allows the flow generator 12 and the controller 14, 16 to be in placed in separate locations.

For example, FIG. 2 illustrates an embodiment wherein the controller 214 is placed on a bedside table 80 and the flow generator 212 is placed under the table 80 away from the controller 214. As illustrated, the controller 214 includes a stand 82 structured to maintain it in a generally upright position on the table 80. Additionally, the controller 214 is structured to function as a clock with an alarm and/or radio. In use, the flow generator 212 can operate under the table 80 where it is concealed and the noise during use is less disturbing to the patient. Meanwhile, the patient can wirelessly control the flow generator 212 by the controller 214 which doubles as an clock, alarm, and/or radio.

Controller with Integral Blood Glucose Monitor

Figure 3:
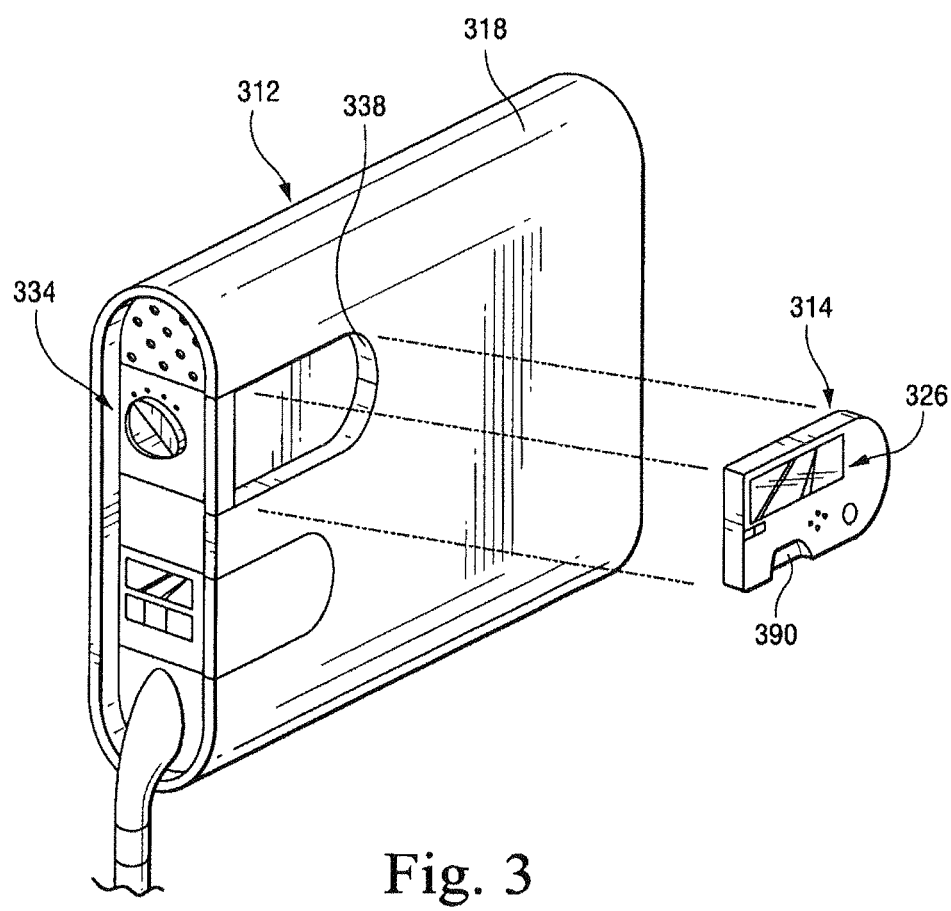
FIG. 3 is a perspective view of an air delivery system constructed according to still another embodiment of the present invention.

FIG. 3 illustrates an arrangement that includes a flow generator 312 and a removably attachable blood glucose monitor 314. The monitor 314 may be stored within a recess 338 provided in the housing 318 of the flow generator 312. As illustrated, the monitor 314 includes a control panel 326 and a recess 390 adapted to receive one of the patient's fingers for performing a blood glucose test. Information from the monitor 314 may be communicated to a physician via the flow generator. In an embodiment, the monitor 314 may adapt therapeutic pressure to optimize patient ventilation according to blood glucose levels.

In the illustrated embodiment, control features 334 for operating the flow generator 312 are provided on the housing 318. However, the control features 334 may be incorporated into the monitor 314 in a manner as described above.

Medicine Delivery Module

In another embodiment, the flow generator may include an add-on or integral medicine delivery module that delivers medicinal drug (e.g., insulin) into the air delivery path. The medicinal drug may include atomized, aerosol, and/or particulate medication, and the medicinal drug may be delivered into the air delivery path anywhere between the flow generator and the patient interface. In an embodiment, the medicine delivery module may be integrated with the controller and a bypass tube may add the drug into the air delivery path.

Input/Output to Couple Flow Generator and Controller

In illustrated embodiments, the controller 14, 214 for the flow generator 12, 212 may be wirelessly communicated with the flow generator 12, 212. However, the controller 14, 214 may be communicated with the flow generator 12, 212 in any other suitable manner.

Figure 4:
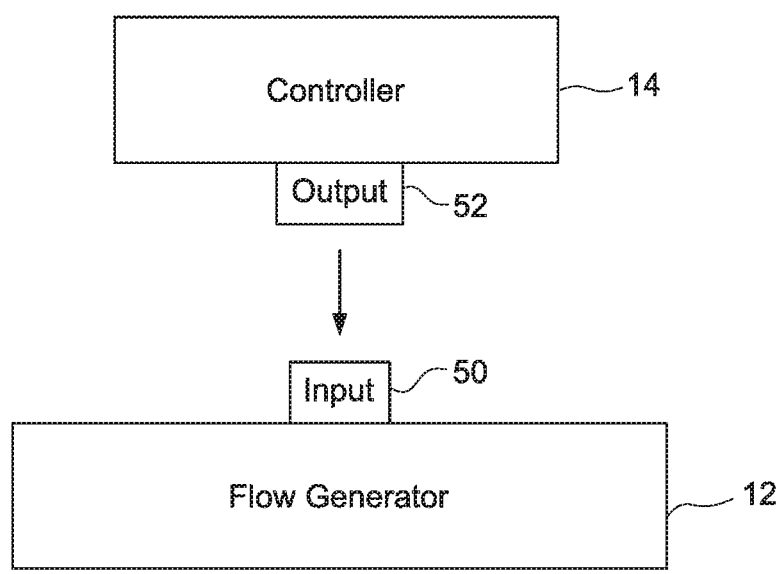
FIG. 4 is a schematic view of an air delivery system constructed according to yet another embodiment of the present invention.

For example, as schematically shown in FIG. 4, the flow generator 12 may include an input 50, and each controller 14 may include an output 52 (e.g., a communication port or an electrical contact) adapted to removably engage the input 50 to communicate each controller 14 with the flow generator 12. In an embodiment, the input may be provided within the recess 38 of the flow generator housing 18 shown in FIG. 1, and the output of the controller removably engages the input when the controller is removably inserted into the recess 38. The system may be disabled if a controller is not properly engaged with the flow generator. In another embodiment, the input and output are coupled via a cable.

Controller and Patient Monitors

The controller may be adapted to receive information from one or more patient monitors monitoring one or more patient parameters, e.g., patient's heart rate, breathing effort, etc. The patient and/or clinician may adjust the operating parameters of the flow generator based on the monitored parameters and/or the flow generator may automatically update the operating parameters based on the monitored parameters.

Programmable Controller

The controller may be programmable to operate other devices, e.g., television, stereo, etc. That is, the controller may be programmed via self learning to function as a remote control for the television, stereo, etc. and may interface with wireless smart wiring in the home to control lighting, etc.

Flow Generator with Single Controller

In an embodiment, the flow generator may be provided with a single removable controller that may be used by the patient and/or clinician. Thus, the controller may form a common unit that incorporates primary and auxiliary controllers. The common unit may be selectively attachable to and detachable from the flow generator in a manner as described above. Moreover, the auxiliary controller may only be accessible using an electronic key, e.g., only available at a health clinic, provided to only a licensed clinician or health provider.

In another embodiment, the single controller may be used by the clinician to program the flow generator, and the flow generator may be supplied to the patient without the controller so the patient cannot adjust the operating parameters.

In still another embodiment, the flow generator and the controller may be sold separately from one another. That is, the patient may purchase the controller separately from the flow generator depending on desired control features and/or treatment. Also, the patient could rent a flow generator when traveling, e.g., overseas, and therefore only travel with the controller which makes travel more convenient.

In yet another embodiment, the flow generator may be upgradable or simply changeable between AUTOSET®

(generically known as auto-adjusting mode), CPAP, VPAP® (generically known as bi-level mode), etc, by using different controllers or a single controller that can select the desired operating mode. That is, the patient can upgrade a basic flow generator that is programmed and structured to operate in a plurality of modes (e.g., AUTOSET®, CPAP, VPAP®, etc., all available from ResMed) by using a new controller, and hence make the flow generator work like an AUTOSET®, CPAP, VPAP®, etc. The flow generator can be upgraded with a hardware upgrade, i.e., using a different controller, and/or a software upgrade, i.e., upgrading software of a single controller.

Controller Usable in Plurality of Flow Generators

In still another embodiment, the flow generator may include a single patient controller and a single technician controller. Moreover, the technician controller may be used in a plurality of flow generators. Thus, the technician may use a single controller to adjust the operating parameters of different flow generators.

Controller with Touchscreen Display

Figure 5B:
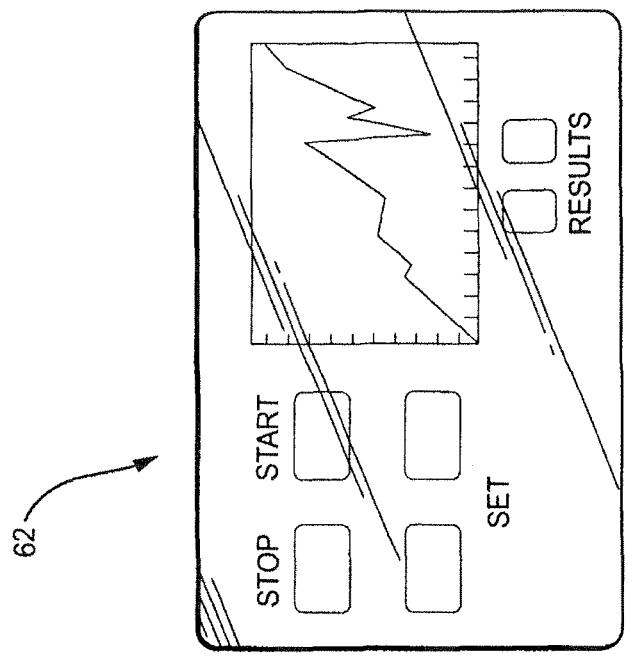
FIG. 5B is a plan view of a touchscreen display configured for an advanced controller according to another embodiment of the present invention.
Figure 5A:
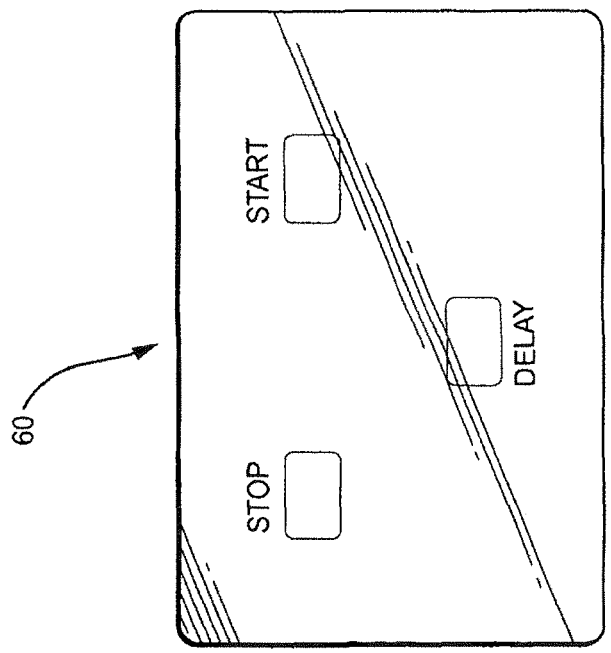
FIG. 5A is a plan view of a touchscreen display configured for a basic controller according to another embodiment of the present invention.

In another embodiment, the controller may have a touchscreen display, which may be configured to display functions for operating certain types of flow generators and/or for certain user levels. The display may include a relatively large touchscreen with a configurable background that shows simple menus and information, and start/stop buttons. The clinician can set up the display to suit the user and/or the user can select which functions need to be displayed, i.e., buttons frequently used by the user. For example, FIG. 5A illustrates an embodiment of a touchscreen display 60 that is configured to include simple functions for a basic controller, and FIG. 5B illustrates an embodiment of a touchscreen display 62 that is configured to include more complex functions for a more advanced controller, e.g., clinician controller.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. An air delivery system, comprising:
   a controllable flow generator operable to generate a supply of pressurized breathable gas to be provided to a patient for treatment; and
   a controller adapted for wireless communication with the flow generator, wherein
   the controller is configured, upon receipt of an electronic key, to control advanced aspects of the flow generator in order to tailor a program of pressurized breathable gas treatment to be provided to the patient; and
   the controller is further configured to control basic aspects of the flow generator in accordance with a tailored treatment program.

2. The air delivery system according to claim 1, wherein the controller is configured to control advanced aspects of the flow generator via a clinical menu.

3. The air delivery system according to claim 1, wherein the controller is configured, upon receipt of the electronic key, to allow access to a memory that stores preferred operating parameters for a plurality of treatment programs.

4. The air delivery system according to claim 1, wherein the controller is configured, upon receipt of the electronic key, to receive operating parameters for the tailored treatment program via one or more control features of the controller.

5. The air delivery system according to claim 1, wherein the controller is configured, upon receipt of the electronic key, to access a log of use of the flow generator by the patient.

6. The air delivery system according to claim 1, wherein the basic aspects of the flow generator comprise start, stop, and delay timer operations of the flow generator.

7. The air delivery system according to claim 1, wherein the controller comprises a touchscreen display.

8. The air delivery system according to claim 7, wherein the controller is configured, upon receipt of the electronic key, to configure the touchscreen display to display simple functions for control of the basic aspects of the flow generator.

9. The air delivery system according to claim 7, wherein the touchscreen display is configured, upon receipt of the electronic key, to display complex functions for control of the advanced aspects of the flow generator.

10. A flow generator operable to generate a supply of pressurized breathable gas to be provided to a patient for treatment, wherein
    the flow generator is configured for wireless communication with a controller configured to control operation of the flow generator to generate the supply of pressurized breathable gas;
    the controller being configured, upon receipt of an electronic key, to control advanced aspects of the flow generator in order to tailor a program of pressurized breathable gas treatment to be provided to the patient; and
    the controller being further configured to control basic aspects of the flow generator in accordance with a tailored treatment program.

11. A method of operating a flow generator, the method comprising:
    receiving, by a controller adapted for wireless communication with the flow generator, an electronic key;
    controlling by the controller, upon receipt of the electronic key, advanced aspects of the flow generator in order to tailor a program of pressurized breathable gas treatment to be provided to a patient by the flow generator; and
    controlling, by the controller, basic aspects of the flow generator in accordance with a tailored treatment program.

12. The air delivery system according to claim 2, wherein the controller is configured, upon receipt of the electronic key, to allow access to a memory that stores preferred operating parameters for a plurality of treatment programs.

13. The air delivery system according to claim 2, wherein the controller is configured, upon receipt of the electronic key, to receive operating parameters for the tailored treatment program via one or more control features of the controller.

14. The air delivery system according to claim 2, wherein the controller is configured, upon receipt of the electronic key, to access a log of use of the flow generator by the patient.

15. The air delivery system according to claim 2, wherein the basic aspects of the flow generator comprise start, stop, and delay timer operations of the flow generator.

16. The air delivery system according to claim 2, wherein the controller comprises a touchscreen display.

* * * * *